United States Patent
Merdan

(10) Patent No.: US 8,044,322 B2
(45) Date of Patent: Oct. 25, 2011

(54) VERTICAL STENT CUTTING PROCESS

(75) Inventor: Kenneth M. Merdan, Greenfield, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 12/914,607

(22) Filed: Oct. 28, 2010

(65) Prior Publication Data

US 2011/0036820 A1 Feb. 17, 2011

Related U.S. Application Data

(63) Continuation of application No. 10/190,975, filed on Jul. 8, 2002, now abandoned.

(51) Int. Cl.
*B23K 26/14* (2006.01)
(52) U.S. Cl. ............ 219/121.67; 219/121.7; 219/121.71
(58) Field of Classification Search ............. 219/121.67, 219/121.7, 121.71
See application file for complete search history.

(56) References Cited

U.S. PATENT DOCUMENTS

| | | | |
|---|---|---|---|
| 3,263,852 A | 8/1966 | Fridrich | |
| 4,335,296 A | 6/1982 | Bredow | |
| 4,424,925 A * | 1/1984 | Rumayor-Aguirre et al. .... | 225/2 |
| 4,607,150 A | 8/1986 | Bannister | |
| 4,618,262 A | 10/1986 | Maydan et al. | |
| 4,694,139 A | 9/1987 | Roder | |
| 4,698,480 A | 10/1987 | Klingel | |
| 4,728,773 A | 3/1988 | Roberts et al. | |
| 4,889,968 A | 12/1989 | Miyama et al. | |
| 4,987,286 A | 1/1991 | Allen | |
| 5,073,694 A | 12/1991 | Tessier et al. | |
| 5,149,937 A | 9/1992 | Babel et al. | |
| 5,267,381 A | 12/1993 | Wright et al. | |
| 5,424,508 A | 6/1995 | Swain et al. | |
| 5,512,078 A | 4/1996 | Griffin | |
| 5,514,154 A | 5/1996 | Lau et al. | |
| 5,628,918 A | 5/1997 | Mastalski | |
| 5,759,192 A | 6/1998 | Saunders | |
| 5,780,807 A | 7/1998 | Saunders | |
| 5,902,499 A | 5/1999 | Richerzhagen | |
| 5,906,759 A | 5/1999 | Richter | |
| 5,922,005 A | 7/1999 | Richter | |
| 5,994,667 A | 11/1999 | Merdan et al. | |
| 6,131,266 A | 10/2000 | Saunders | |
| 6,197,048 B1 | 3/2001 | Richter | |
| 6,403,916 B1 | 6/2002 | Spooner et al. | |
| 6,586,705 B1 | 7/2003 | Schell | |
| 6,608,277 B2 | 8/2003 | Spooner et al. | |
| 6,664,499 B1 | 12/2003 | Brink et al. | |
| 6,927,359 B2 | 8/2005 | Kleine et al. | |

FOREIGN PATENT DOCUMENTS

EP 0627277 A1 12/1994

* cited by examiner

*Primary Examiner* — Jessica L Ward
*Assistant Examiner* — Nicholas D'Aniello
(74) *Attorney, Agent, or Firm* — Seager, Tufte & Wickhem LLC

(57) ABSTRACT

A system and method for processing a tubular member for producing a medical device, wherein the tubular member is oriented in a longitudinally vertical position during processing.

18 Claims, 5 Drawing Sheets

VERTICAL STENT CUTTING PROCESS

CROSS-REFERENCE TO RELATED APPLICATIONS

This application is a continuation of U.S. application Ser. No. 10/190,975 filed Jul. 8, 2002.

STATEMENT REGARDING FEDERALLY SPONSORED RESEARCH

Not Applicable

BACKGROUND OF THE INVENTION

A stent is a radially expandable endoprosthesis which is adapted to be implanted in a body lumen. Stents are typically used in the treatment of atherosclerotic stenosis in blood vessels and the like to reinforce body vessels and to prevent restenosis following angioplasty in the vascular system. They have also been implanted in urinary tracts, bile ducts and other bodily lumen. They may be self-expanding or expanded by an internal radial force, such as when mounted on a balloon.

Delivery and implantation of a stent is accomplished by disposing the stent about a distal portion of the catheter, percutaneously inserting the distal portion of the catheter in a bodily vessel, advancing the catheter in the bodily lumen to a desired location, expanding the stent and removing the catheter from the lumen. In the case of a balloon expandable stent, the stent is mounted about a balloon disposed on the catheter and expanded by inflating the balloon. The balloon may then be deflated and the catheter withdrawn. In the case of a self-expanding stent, the stent may be held in place on the catheter via a retractable sheath. When the stent is in a desired bodily location, the sheath may be withdrawn allowing the stent to self-expand.

In the past, stents have been generally tubular but have been composed of many configurations and have been made of many materials, including metals and plastic. Ordinary metals such as stainless steel have been used as have shape memory metals such as Nitinol and the like. Stents have also been made of bio-absorbable plastic materials. Stents have been formed from wire, tube stock, etc. Stents have also been made from sheets of material which are rolled.

A number of techniques have been suggested for the fabrication of stents from sheets and tubes. One such technique involves laser cutting a pattern into a sheet of material and rolling the sheet into a tube or directly laser cutting the desired pattern into a tube. Other techniques involve cutting a desired pattern into a sheet or a tube via chemical etching or electrical discharge machining.

Laser cutting of stents has been described in a number of publications including U.S. Pat. No. 5,780,807 to Saunders, U.S. Pat. No. 5,922,005 to Richter and U.S. Pat. No. 5,906,759 to Richter. Other references wherein laser cutting of stents is described include: U.S. Pat. Nos. 5,514,154, 5,759,192, 6,131,266 and 6,197,048.

An example of a conventional laser for cutting a stent is a highly focused pulsed Nd:YAG laser which has a pulse duration in the range of approximately 0.1 to 20 milliseconds. This is a long pulse time for cutting and characteristically produces a relatively large melt zone and heat affected zone (HAZ) on the metal. The conventional laser cutting process typically results in the formation of melt dross on the inside edge of the cut tube. This dross must be cleaned off in subsequent processes.

Past laser cutting systems typically mount the tube to be cut from a spindle shaft in a horizontal orientation wherein the laser is mounted perpendicular to the longitudinal axis of the tube in a downward looking configuration. Such a horizontal orientation of the stent tube has many drawbacks.

For example, as the tube is being cut, dross and other debris may accumulate in the tube interior. This requires a stream of water to flush the tube to wash away the debris. The horizontal orientation of the tube additionally exacerbates the problem of ridding debris from the tube as debris must be actively driven out the open end of the tube. This necessitates the flushing stream be applied with significant pressure to ensure that debris does not clog the tube end.

Another more serious drawback is that in some cases, particularly in longer tubes, the tube may tend to bow as a result of gravity. Such bowing may interfere with the precise nature of the stent cutting process, resulting in cutting errors or more significant damage to the tube/stent. In addition, as the tube is rotated during cutting, any bowing of the tube will cause the unsecured end of the tube to oscillate resulting in excess strain being placed on the tube, and potentially leading to improper cutting and/or the formation of cutting imperfections.

In light of the above a need exists to provide a laser cutting/processing system wherein the potential for tube bowing and tube oscillation is minimized or removed completely, and where cutting debris such as melt dross is more easily and consistently removed from the tube during processing.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. In at least one embodiment the invention is directed to a system for cutting, etching and/or otherwise processing a hollow metal tube for manufacturing a stent, wherein the tube/stent is positioned with its longitudinal axis in a vertical orientation relative to the ground. Such vertical orientation allows gravity to help maintain at least the free end the tube/stent in a stable position through out the cutting process.

In some embodiments of the invention the tube being cut may be at least partially, and even entirely, constructed of a polymer.

Vertical orientation of the tube also encourages dross and other debris formed during cutting to be gravitationally drawn out of and away from the tube continuously through out the laser cutting process.

In some embodiments a stream of fluid or other media may be poured or injected through the lumen of the tube to cool the tube, provide increased stability to the tube, and/or assist in removing debris from the tube.

As indicated above, in some embodiments the tube is cut or machined by a laser, such as a YAG, IR, UV, diode, $CO_2$ or other type of laser. In at least one embodiment the stent cutting system utilizes a hybrid laser/water jet mechanism to direct laser energy to the tube through a column of fluid such as water. Such laser/water jet systems are known and are commercially available from SYNOVA Inc., of Lausanne, Switzerland. The SYNOVA system utilizes a laser beam that is contained within a water jet as a parallel beam, similar in principle to an optical fiber.

In some embodiments the flow of fluid or other media through the tube lumen will help protect the tube interior from potential damage caused by the cutting laser by disrupting the water jet and laser energy transmitted therethrough. Such use of a media flow in conjunction with a laser/water jet hybrid system is described in greater detail in a co-pending patent application filed simultaneously herewith entitled Tubular Cutting Process and System.

In some embodiments a collar or guide defines a chamber which at least a portion of the free end of the tube is inserted. The guide may be utilized to stabilize and/or minimize oscillations or other disruptive movement of the free end of the tube during the cutting process.

In some embodiments a nozzle or other attachment sprays a fluid onto and/or through the tube.

Where a fluid is sprayed or otherwise directed onto or through the tube, the fluid may be act as an oxidizer, cleaner, polishing agent, pretreatment or other solution. In some embodiments the fluid aids in removing debris from the tube during processing.

In various embodiments the guide and the chamber defined thereby, may have a variety of shapes and sizes to accommodate tubes of different configurations. In at least one embodiment the guide is split, having at least two portions. The portions may be variably positioned to allow the guide to receive a wide variety of tube diameters therein.

In at least one embodiment the guide is one or more coils of a formed wire(s) which are disposed about at least a portion of the tube.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
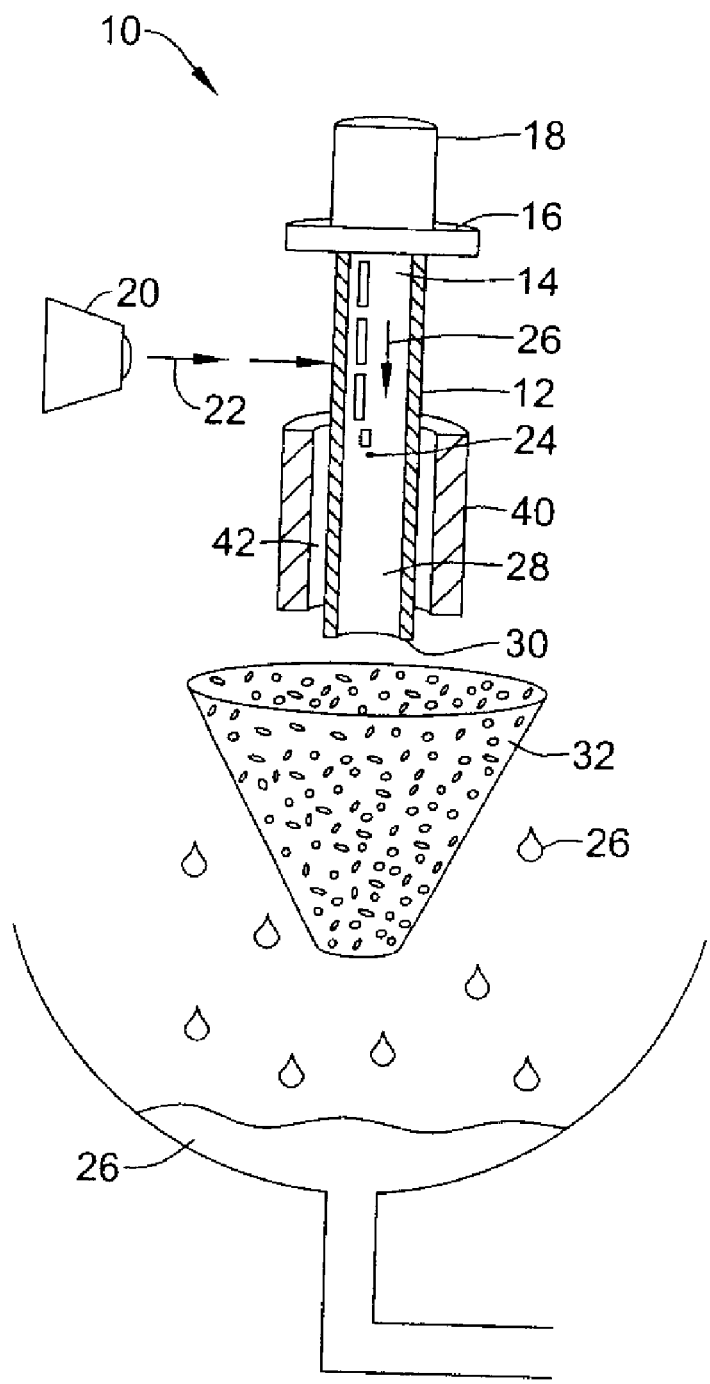
FIG. 1 is a side view of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above the present invention is directed to a variety of embodiments. In at least one embodiment, shown in FIG. 1, the invention is directed to a mechanism (system), indicated generally at 10, for processing and/or cutting a hollow tubular body 12 into a medical device such as a stent.

In the embodiment shown, the hollow tubular body 12 may be any type of tube suitable for laser processing and/or cutting. Such a tube 12 may be a tubular member suitable for the construction of a stent, graft, stent-graft, vena cava filter, hypo tube, catheter or component thereof, or any other device suitable for insertion and/or implantation into a body lumen. Where the tube 12 is intended for the construction of a stent, the tube 12 will typically be at least partially constructed from a metal such as stainless steel, nickel, titanium, palladium, gold, tantalum, or any other metal or alloy thereof. However, other materials may be alternatively or additionally used, such as one or more polymers. In at least one embodiment tube 12 is constructed of a nickel-titanium alloy such as nitinol.

Where tube 12 is at least partially constructed from one or more polymer substances, the substances may include, but are not limited to the following examples: polyester/polyether elastomers such as Arnitel™ available from DSM Engineering; polyurethane-polyether polymers, such as Tecothane™ and/or Tecoplastm both being available from Thermedics, Inc.; polyester-polyurethanes, such as Pellethane™ sold by Dow Chemical; polyester-polyurethanes, such as Estane sold by BF Goodrich; polyether block amides (PEBA), such as Pebax™ available from Elf Atochem; styrene15 butadien-styrene triblock copolymers, such as Kraton™ sold by Shell Chemical company; styrenic block copolymers; polyurethanes; silicone rubber; natural rubber; copolyesters; polyamides; EPDM rubber/polyolefin; nitril rubber/PVC; fluoroelastomers; butyl rubber; epichlorohydrin; block copolymers; polyethylene terephthalate (PET); polyethylene naphthalate (PEN); polybutylene terephthalate (PBT); polytrimethylene terephthalate (PTT); poly lactic acid (PLA); fluoropolymers; polyolefins; polystyrene; polyvinyl chloride (PVC); acrylonitrile-butadiene-styrene polymers; polyacrylonitrile; polyacrylate; vinyl acetate polymer; cellulose plastics; polyacetal; polyethers; polycarbonates; polyphenylene sulfide; polyarylethersulfones; polyaryletherketones; polytetrafluoroethylene; polyamide copolymer, such as MXD6™ available from Mitsubishi Gas Chemical Co. or Cristamid™ available from Atofina; shape-memory polymers; liquid crystal polymers; bio-absorbable polymers; radiopaque polymers; MRI-visible polymers; etc.

Tube 12 may also include various coatings or surface materials, such as drug and/or drug vectors, lubricants, etc.

Regardless of the particular composition or the type of material used for tube 12, in accordance with the present invention the tube is processed or cut while positioned in a substantially longitudinal vertical orientation, such as is shown. Longitudinally vertical position as used herein means that tube is positioned relative to the ground such that the longitudinal axis of the tube is substantially perpendicular to the plane of the ground.

Vertical orientation of the tube during the cutting process provides an increase in processing efficiency, particularly by employing gravity to prevent tube bowing, encourage dross removal from the tube, and reduce oscillations at the free end of the tube as it rotates.

In the embodiment shown the tube 12 is mounted at a first end 14 to a affixing device 16 of a rotary spindle or shaft 18 of a processing mechanism. During the cutting process the shaft maybe rotated as well as moved vertically in an upwards and/or downwards direction according to a predetermined pattern. The movement of the shaft 18 causes the tube 12 to be moved relative to a laser or other cutting mechanism 20.

In some embodiments the laser 20 may be moveable relative to the tube 12. In some embodiments the laser 20 may be capable of directing laser energy, indicated by arrow 22, to the tube 12 from multiple angles and/or directions.

In the embodiment shown in FIG. 1, laser 20 directs laser energy 22 to the tube 12. As tube 12 is moved via the predetermined movement pattern of shaft 18 the laser energy 22 cuts a corresponding pattern into the tube 12. As indicated above laser 20 may be any type of laser, such as a YAG, diode, IR, UV, $CO_2$, or other type of laser. In at least one embodiment laser 20 is a hybrid laser/water jet such as is available from SYNOVA Inc., of Lausanne, Switzerland and described in co-filed U.S. patent application entitled Tubular Cutting Process and System.

Where laser 20 is a laser/water jet hybrid, in some embodiments the vertical orientation of the tube 12 will help prevent damage to the tube interior as gravity will tend to draw the water column down and thus deflect the laser energy contained therein. Deflection of the laser energy may be further encouraged by applying a fluid or media flow through the tube interior such as is described in greater detail below.

During the cutting process dross and other debris particles 24 are formed. The unique orientation of the tube 12 will assist in the removal of dross from the tube 12 as gravitational pull will tend to draw the dross downward and out of the tube 12. A flow of fluid, such as a gas, liquid solution, suspension or other media, indicated by arrow 26 and hereinafter referred to as a media flow, may be applied to the tube to further encourage removal of debris 24. Media flow 26 may also act to cool the tube 12 during processing.

In some embodiments, the media flow 26 is directed through the lumen 28 that the hollow tube 12 defines. Dross and other debris particles 24 that extend into the lumen 28 may be caught in the media flow 26 and pass through the lumen 28 out the free end 30 of the tube 12. In some embodiments waste particles, such as debris 24 may be collected in a filter 32 which allows media flow 26 to pass therethrough for reclamation or disposal. Filter 32 may also be utilized to receive the tubular member 12 following processing.

In some embodiments, media flow 26 may be directed to any portion or surface of the tube 12.

The vertical orientation of the tube 12 allows system 10 to operate by using gravity to drive media flow 26 through tube 12. However, if desired media flow 26 may be applied under any desired pressure.

As indicated above, in prior horizontal orientation tube cutting systems, bowing of the tube during the cutting process may result in significant damage to the tube resulting in the final stent product being improperly cut. The vertical orientation employed by the present system 10 avoids bowing of the tube 12 as gravity will tend to keep the tube in its natural straight orientation. However, it is recognized that in some cases the free end 30 of the tube 12 or portions thereof, will whip or oscillate as the tube 12 is spun and moved in accordance with the predetermined cutting pattern. Such unrestricted movement may be detrimental to accurate cutting.

To ensure that such unrestricted movement is minimized or prevented, some embodiments of the present invention include a guide mechanism or collar 40. Guide 40 is a tubular member which defines a guide chamber 42 into which the free end 30 of the tube 12 or a portion thereof, is inserted. Preferably guide 40 is fixedly mounted to a surface of mechanism 10, but in some embodiments the guide may moveable relative to the tube 12. During processing of the tube 12 the guide 40 prevents the free end 30 of the tube 12 from experiencing excessive horizontal movement outside the scope of the predetermined cutting pattern.

Figure 2:
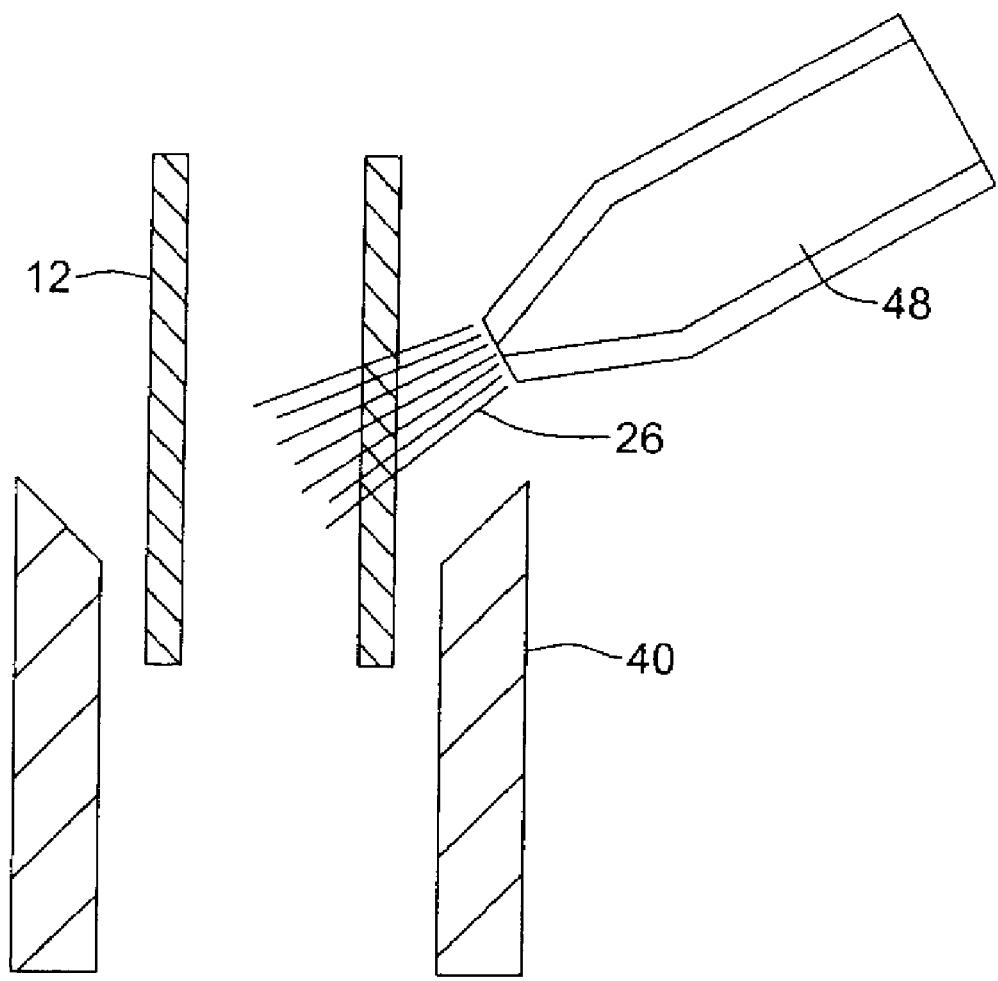
FIG. 2 is a cross-sectional view of an example of a guide mechanism.

In another embodiment shown in FIG. 2, a fluid nozzle 48 may be positioned adjacent to the guide 40. Nozzle 48 is utilized to inject media flow 26 into and/or around tube 12 during processing.

In some embodiments media flow 26 may also act as a lubricant, oxidizer, cleaner, polishing agent, and/or pretreatment.

In the embodiments shown in FIG. 2, the media flow 22 directed through or adjacent to the guide 40 may replace or be supplementary to other media flows such as have been previously described in relation to FIG. 1.

Guide 40 may have a variety of configurations and functions. For example, in the embodiments shown in FIGS. 3-5 a guide 40 having a variable diameter to accommodate tubes of different diameters is shown. In the embodiment shown, the guide 40 comprises two portions 54 and 56 that may be moved toward or away from each other to allow securement of a tube 12 of a larger diameter or a tube 12 of a smaller diameter with equal ease such as is illustrated in FIGS. 4 and 5 respectively.

Figure 3:
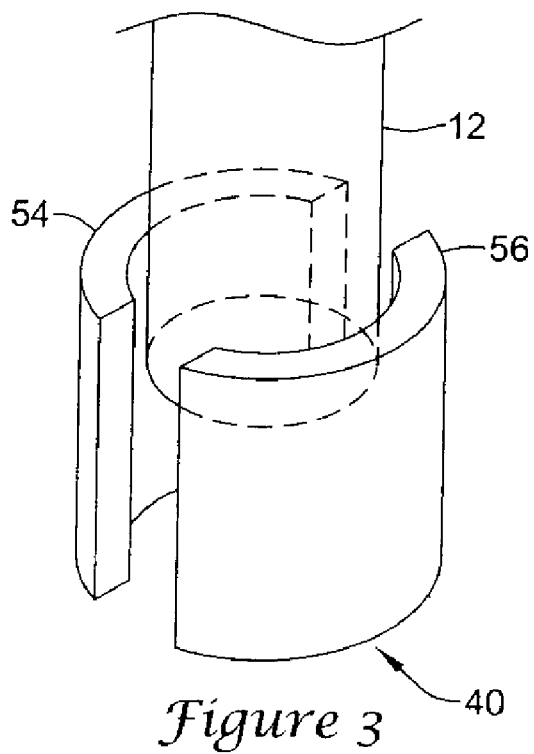
FIG. 3 is a perspective view of an example of a variable diameter guide mechanism.
Figure 4:
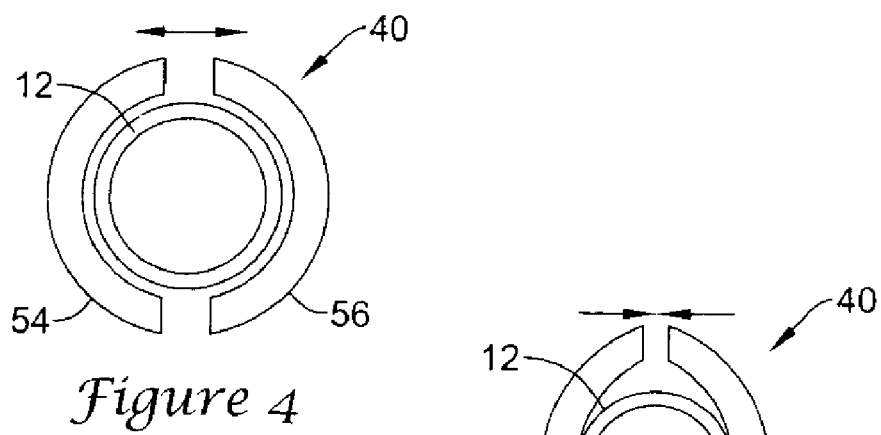
FIG. 4 is a top down cross-sectional view of the guide mechanism of FIG. 3 shown in use with a tube of a first diameter.
Figure 5:
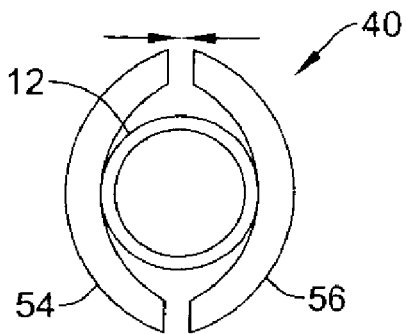
FIG. 5 is a top down cross-sectional view of the guide mechanism of FIG. 3 shown in use with a tube of a second diameter.

It must noted that the two component configuration of a guide 40 shown in FIGS. 3-5 represents merely one embodiment of the guide 40. As desired, a variable diameter guide 40 may be equipped with any number of portions or movement mechanisms. Additionally the guide portions 54 and 56 may be provided with a variety of shapes, some examples of which are shown in FIGS. 6-9.

Figure 6:
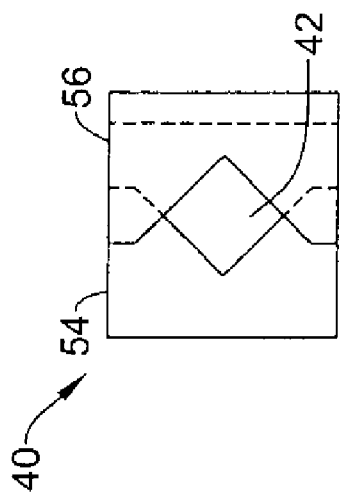
FIGS. 6 and 7 show an example shape of a guide mechanism.
Figure 7:
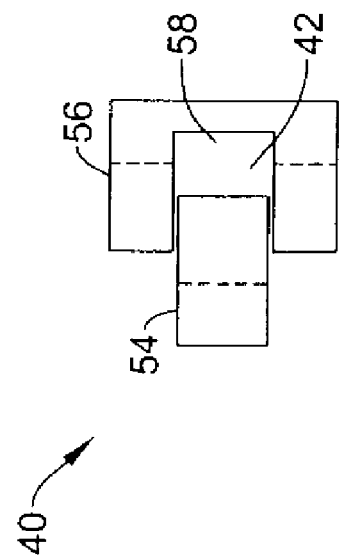

In FIGS. 6 and 7 a variable diameter guide 40 is shown wherein the chamber 42 comprises a diamond shape that may be expanded or contracted in the manner shown.

Figure 8:
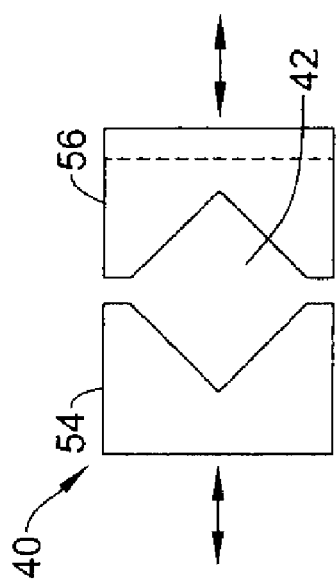
FIGS. 8 and 9 show an example shape of a guide mechanism.
Figure 9:
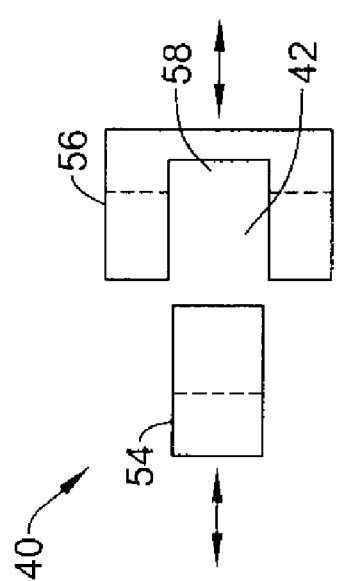

In FIGS. 8 and 9 another embodiment of the variable diameter guide 40 is shown wherein a first portion 54 defines a slot 58 into which the second portion 56 is inserted to form the chamber 42.

Figure 10:
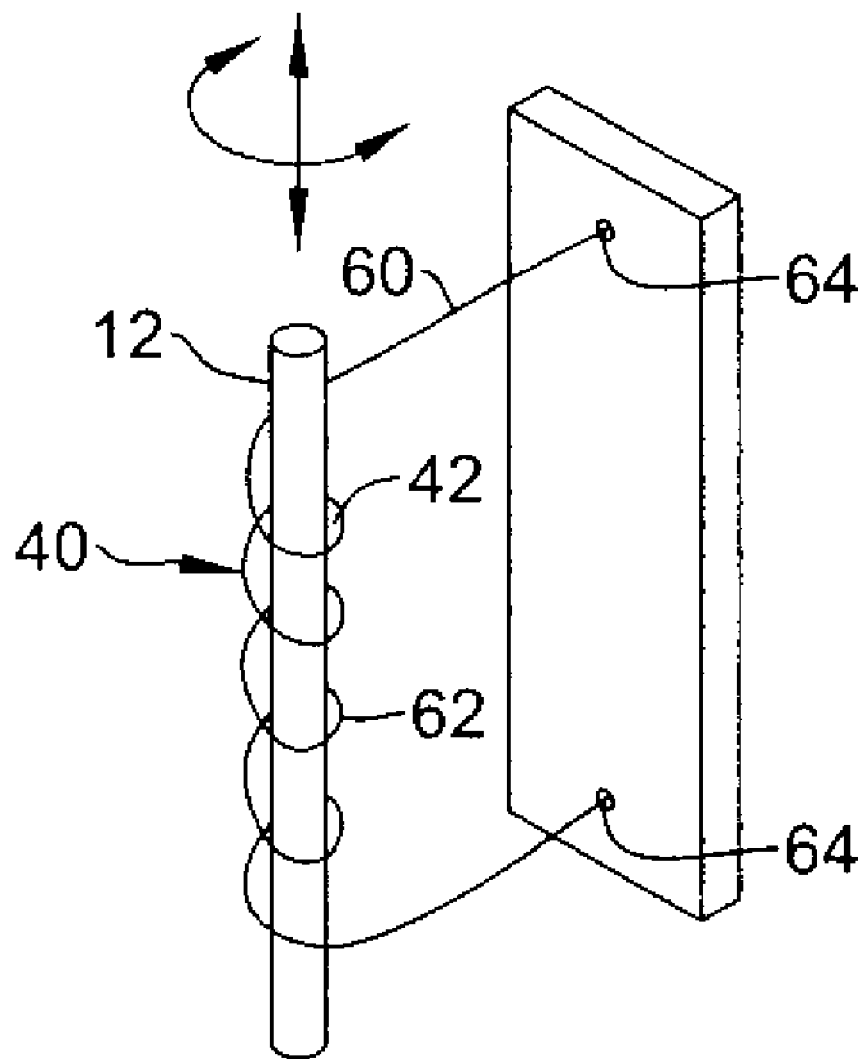
FIG. 10 shows another example of a guide mechanism.

In yet another embodiment, shown in FIG. 10, the guide 40 may comprise a wire 60 having one or more coils 62 which define the chamber 42 into which the tube 12 is inserted. The coils 62 of the wire may be contracted or expanded merely by increasing or releasing tension on the wire ends 64.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method for removing material from a wall of a tubular member to form a plurality of holes therethrough according to a predetermined pattern, the method comprising:
   obtaining an optical system including a laser, and a securement device adapted to mount the tubular member;
   wherein the optical system is adapted to form a cutting spot on a wall of a tubular member, said cutting spot having sufficient energy to penetrate the wall of the tubular member, and to modulate the laser energy according to a predetermined pattern thereby forming a plurality of holes through the tubular member;
   mounting terminal end of the tubular member to the securement device such that a cylindrical axis of the tubular member is held in a vertical orientation while leaving the entire cross section of a lowermost terminal end of the tubular member unobstructed;
   forming a cutting spot on the wall of the tubular member;
   moving at least one of the optical system and the securement device while maintaining the cutting spot on the wall of the tubular member thereby moving the cutting spot over at least a portion of the wall of the tubular member in both vertical and circumferential directions; and
   directing a media flow, the media flow being a fluid, through a lumen defined by the tubular member from the uppermost end to the lowermost end.

2. The method of claim 1 further comprising inserting at least a portion of the tubular member into a guide mechanism defining a guide chamber.

3. The method of claim 1 wherein directing the media flow comprises directing the media flow through the lumen defined by the tubular member and about the tubular member.

4. The method of claim 1 wherein the fluid is selected from at least one member of the group consisting of: a gas, a liquid, a liquid solution, a suspension and any combination thereof.

5. The method of claim 2 wherein the guide chamber has a variable diameter.

6. The method of claim 5 wherein the guide mechanism comprises at least two portions, the at least two portions being moveable relative to one another to provide for the variable diameter of the guide chamber.

7. The method of claim 6 wherein the at least two portions define a guide chamber having a substantially circular cross section.

8. The method of claim 6 wherein the at least two portions define a guide chamber having a substantially diamond shaped cross section.

9. The method of claim 6 wherein the guide chamber defines an adjustable slot.

10. The method of claim 1 wherein the securement device is engaged to a drive shaft.

11. The method of claim 1 wherein the laser is selected from at least one member of the group consisting of YAG lasers, diode lasers, $CO_2$ lasers, IR lasers, laser/water jet hybrids and any combinations thereof.

12. The method of claim 1 wherein a media flow is configured to remove debris buildup within the tubular member.

13. The method of claim 1 wherein the media flow configured to cool the metallic tubular member during removal of the material therefrom.

14. The method of claim 1 wherein the media flow is selected from at least one member of the group consisting of: lubricants, oxidizers, cleaners, polishing agents, pretreatments, and any combination thereof.

15. A method for manufacturing a metallic tubular member comprising:
   obtaining a laser apparatus and a securement device adapted to mount a metallic tubular member;
   wherein the laser apparatus is adapted to selectively remove material from the metallic tubular member thereby forming a plurality of holes through the metallic tubular member according to a predetermined pattern;
   mounting the metallic tubular member to the securement device such that the metallic tubular member is held by an uppermost terminal end of the metallic tubular member with a cylindrical axis of the metallic tubular member in a vertical orientation while leaving the entire cross section of a lowermost terminal end of the metallic tubular member unobstructed;
   moving at least one of the laser apparatus and the securement device whereby the laser system removes material from at least a portion of the wall of the tubular member in both vertical and circumferential directions; and
   directing a media flow comprising a fluid into the uppermost end of the metallic tubular member, the media flow directed through a lumen defined by the metallic tubular member and out the lowermost end.

16. The method of claim 15, further comprising collecting the fluid in a fluid reservoir positioned below the lower end of the metallic tubular member.

17. The method of claim 16, further comprising filtering material removed from the metallic tubular member from the fluid.

18. The method of claim 15 further comprising inserting the metallic tubular member into a guide chamber;
   wherein the guide chamber is sized and configured such that when the metallic tubular member is substantially straight, inserting the metallic tubular member into the guide chamber forms an annular space between the metallic tubular member and the guide chamber.

* * * * *

UNITED STATES PATENT AND TRADEMARK OFFICE
CERTIFICATE OF CORRECTION

PATENT NO. : 8,044,322 B2
APPLICATION NO. : 12/914607
DATED : October 25, 2011
INVENTOR(S) : Kenneth M. Merdan It is certified that error appears in the above-identified patent and that said Letters Patent is hereby corrected as shown below:

Column 7, line 32, claim 1: after the word "mounting", add "an uppermost"

Signed and Sealed this
Sixth Day of March, 2012

David J. Kappos
*Director of the United States Patent and Trademark Office*